US010196153B2

(12) United States Patent
Lamberti et al.

(10) Patent No.: US 10,196,153 B2
(45) Date of Patent: Feb. 5, 2019

(54) METHOD OF MONITORING A COMPOSITE MATERIAL

(71) Applicant: LEONARDO S.p.A., Rome (IT)

(72) Inventors: Patrizia Lamberti, Nocera Inferiore (IT); Giovanni Spinelli, Fisciano (IT); Vincenzo Tucci, Naples (IT); Luigi Vertuccio, Mercato San Severino (IT); Liberata Guadagno, Fisciano (IT); Salvatore Russo, Quarto (IT); Generoso Iannuzzo, Avellino (IT)

(73) Assignee: LEONARDO S.p.A., Rome (IT)

( * ) Notice: Subject to any disclaimer, the term of this patent is extended or adjusted under 35 U.S.C. 154(b) by 0 days.

(21) Appl. No.: 15/496,367

(22) Filed: Apr. 25, 2017

(65) Prior Publication Data

US 2017/0313436 A1 Nov. 2, 2017

(30) Foreign Application Priority Data

Apr. 27, 2016 (IT) ................. 10201642740

(51) Int. Cl.
*G01B 7/16* (2006.01)
*G01M 5/00* (2006.01)
*B64D 45/00* (2006.01)
*G01N 27/04* (2006.01)
*G01N 27/20* (2006.01)

(52) U.S. Cl.
CPC ............ *B64D 45/00* (2013.01); *G01B 7/18* (2013.01); *G01M 5/0041* (2013.01); *G01M 5/0083* (2013.01); *G01N 27/041* (2013.01); *G01N 27/20* (2013.01); *B64D 2045/0085* (2013.01)

(58) Field of Classification Search
CPC ....... B64D 45/00; G01B 7/18; G01M 5/0041; G01M 5/0083; G01N 27/20; G01N 27/041

USPC ......................................................... 340/945
See application file for complete search history.

(56) References Cited

U.S. PATENT DOCUMENTS

| 7,786,736 B2 * | 8/2010 | Thostenson ......... B29C 47/0004 324/525 |
| 7,908,928 B2 * | 3/2011 | Vik ..................... G01M 5/0033 73/806 |
| 8,384,398 B2 | 2/2013 | Laflamme et al. |

(Continued)

FOREIGN PATENT DOCUMENTS

| CA | 2 570 117 | 1/2006 |
| CA | 2 766 486 | 7/2010 |

OTHER PUBLICATIONS

European Search Report, European Patent Application No. 17167744. 6, European Patent Office, dated Sep. 26, 2017.

(Continued)

*Primary Examiner* — Steven Lim
*Assistant Examiner* — Mancil Littlejohn, Jr.
(74) *Attorney, Agent, or Firm* — Valauskas Corder LLC

(57) ABSTRACT

The method allows to monitor a composite material comprising an epoxy resin filled with electrically conductive nanoparticles, wherein at least one electrical property i.e. impedance of the composite material is influenced by being subjected to a mechanical deformation. The method provides for inserting the composite material in an electric circuit emitting an electric signal whose value depends on the electrical property, so that, when the value of the signal overcomes a given threshold value, a warning message is delivered.

20 Claims, 12 Drawing Sheets

(56) References Cited

U.S. PATENT DOCUMENTS

| | | | | |
|---|---|---|---|---|
| 9,194,832 B2* | 11/2015 | Dunleavy | ............ | B82Y 30/00 |
| 2008/0231294 A1* | 9/2008 | You | ............ | G01N 27/02 |
| | | | | 324/725 |
| 2011/0142091 A1 | 6/2011 | Wardle et al. | | |
| 2011/0226066 A1* | 9/2011 | Anand | ............ | G01B 7/18 |
| | | | | 73/777 |
| 2013/0280636 A1* | 10/2013 | Kim | ............ | B82Y 30/00 |
| | | | | 429/482 |
| 2013/0312535 A1 | 11/2013 | Dunleavy et al. | | |

OTHER PUBLICATIONS

M. Pour-Ghaz, J. Weiss.; Detecting the time and location of cracks using electrically conductive surfaces. Cement and Concrete Composites, vol. 33, Issue 1, Jan. 2011, pp. 116-123.

\* cited by examiner

METHOD OF MONITORING A COMPOSITE MATERIAL

CROSS-REFERENCE TO RELATED APPLICATIONS

The present invention claims priority to Italian Patent Application No. 02016000042740 Filed on Apr. 27, 2016.

FIELD OF THE INVENTION

The present invention relates to the application of a structural resin filled with electrically conductive nanoparticles, such as carbon nanotubes, as embedded sensor having self-diagnostic functionalities, in particular for applications in the aeronautic field.

BACKGROUND OF THE INVENTION

Health monitoring of structures which are used for long-term and especially in harsh conditions has become increasingly important. Perfect functionality and mechanical integrity are fundamental requirements for structural parts of aircraft that over time can suffer from defects like fractures and fatigue microcracks. As a consequence, if such defects are over-looked, the efficiency of material is strongly compromised and may result in dangerous accidents. Therefore, structural health monitoring (SHM) of fundamental parts of aircrafts (i.e. fuselage, wings, cockpit) that are constantly exposed to threatening environmental effects such as temperature changes, impact by birds or hailstones, lightning strikes, is crucial in order to ensure the safety, serviceability and reliability of the vehicles. At present, the monitoring of such structures, mainly based on non-destructive testing (NDT), such as a X-ray and ultrasonic inspection, acceleration-based modal testing, is time consuming and expensive specially for the structures to be monitored that must be disassembled and transported to testing facilities. For years, the integration of functional components as strain sensors within composite materials has been a challenge in material science as alternative to classical technique. The goal is the development of an embedded strain sensing system in a composite structure having both functions of structural damage identification and sensor self-diagnosis. In situ stress and strain detection, together with structural health monitoring, would provide improved durability and safety of composite structures. An attempt in this direction is disclosed by U.S. Pat. No. 8,384,398 B2 that provides a structural health monitoring in order to localize crack damage in the monitoring of civil structures and infrastructures (such as buildings, bridges, tunnels) by means of one or more capacitive sensor to be applied as sensing skin on the area of interest to be monitored. In the field of nanocomposites, patent CA 2 570 117 C provides a sensing system formed from a conductive ink containing carbon nanofibers and a polymeric resin that must be applied directly to the structure to be monitored in the form of a grid pattern. Damage to the structure may be evaluated in terms of resistance values detected from the sensor in agreement with the classical real-time sensing approach based on piezoresistive material placed on the monitored structure surface and on the detection of the strain-induced electric charge or current, that however suffers from high cost, small sensing area and low durability due to the poor adhesive properties between the parts not able to ensure that the sensor does not peel over the time.

US 2013/0312535 discloses a method for monitoring the health of a structure by applying thereto a sprayable paint formulation, whose variations of electrical resistance under mechanical stress are measured. Hence, the structure to be monitored and the coating paint on which measurements are effected are neatly distinguished.

An object of the present invention is therefore providing an enhanced method of sensing and monitoring in composite materials dangerous stresses, which might even bring about catastrophic failures.

SUMMARY OF THE INVENTION

The above-captioned object is attained by a method according to claim 1 which follows. Preferred features of the method of the invention are disclosed in the dependent claims.

The invention concerns a smart sensor that, by exploiting the piezoresistive properties of the composite material, provides real-time health-monitoring information about its structural integrity. In other words, no additional coatings/layers have to be applied to the structure to be monitored. The invention results particularly attractive in aeronautic engineering field, where the structural health monitoring of some delicate parts of aircrafts may ensure the serviceability and reliability of the same structures, which is an indispensable requirement for the flight safety.

Accordingly, the present invention provides for the application in the aircraft field of a composite material having self-diagnostic functionalities, using the piezoresistive properties of the material to achieve real-time health-monitoring information about its structural integrity.

It has to be emphasized that the method of the invention is very effective under the point of view of the prevention of failure. It may indeed deliver a warning message when a crack as small as 1 nm—preferably up to 5 nm—(and, as such, not yet able to seriously compromise the mechanical properties of the structure) is formed.

Also, the method of the invention measuring electrical impedance under low tension and AC has the advantages of being both more sensible and less dissipative than other methods providing for measuring different electrical parameters.

Preferably, the Young's modulus of the composite material is in the range 500 to 3000 MPa at room temperature. In any case, the composite material may have a much higher elastic modulus, e.g. a storage modulus in the order of tens of GPa.

The inclusion of carbon nanotubes (CNTs) in polymers, even at low weight concentrations, due to their tendency to easily form electrically conductive networks, may impart piezoresistive properties to the resulting nanostructured composite leading to sensing capabilities. In fact, a correlation between the mechanical deformations and the electrical properties of CNT-based composites evaluated in terms of resistance or impedance changes respect to the steady-state electrical value that the material shows in absence of any strain can be evaluated. Moreover, filled polymers can be designed to have specific and tailored properties, thus offering many advantages in comparison to conventional materials based on electro-active polymers or piezoelectric ceramics which present different limitations due to their fragility, non-negligible weight and high voltage or current required for their proper use. The composite material widely adopted as structural part in the aircraft design, shows stimuli-responsive properties suitable for health-structural monitoring purposes. In particular, when the crosshead of the testing systems returns to the initial position, for lower levels of strain that fall in the elastic response of the material, the monitored electrical parameter (resistance or impedance) returns to zero, indicating that significant permanent deformation or irreversible damage has not occurred in the composite. Otherwise, for higher value of tensile strain, when the deformation exceed the elastic response of the sample evolving toward the plastic one, it can be noted a change in resistance/impedance value that start to become irreversible for unloaded sample. In particular, the presence of a residual resistance/impedance appears due to some damage in the sensor most likely as a result of a permanent and irreversible phenomena (yielding) in electrical percolating network associated to morphological rearrangement of the CNTs dispersed in the polymer resin and to the fatigue and plastic deformation of the latter. Therefore, in plastic regime the sensor system may allow the detection of possible damages in the monitored part. In order to quickly locate a small and imperceptible permanent deformation of the material respect to the original condition, the variation of the electrical resistance or impedance of the nanocomposites may be suitably converted into a voltage signal (e.g. by conventional means, such as a Wheastone bridge, instrumentation amplifier, etc.) in order to drive indicator lamps or audible warning devices which will be activated on the basis of the undergone deformation of the structure.

BRIEF DESCRIPTION OF THE DRAWINGS

Methods according to the invention are now provided by way of illustrative, non-limiting examples with reference to the following drawing tables, wherein.

DETAILED DESCRIPTION OF THE INVENTION

Materials and Methods

Figure 1:
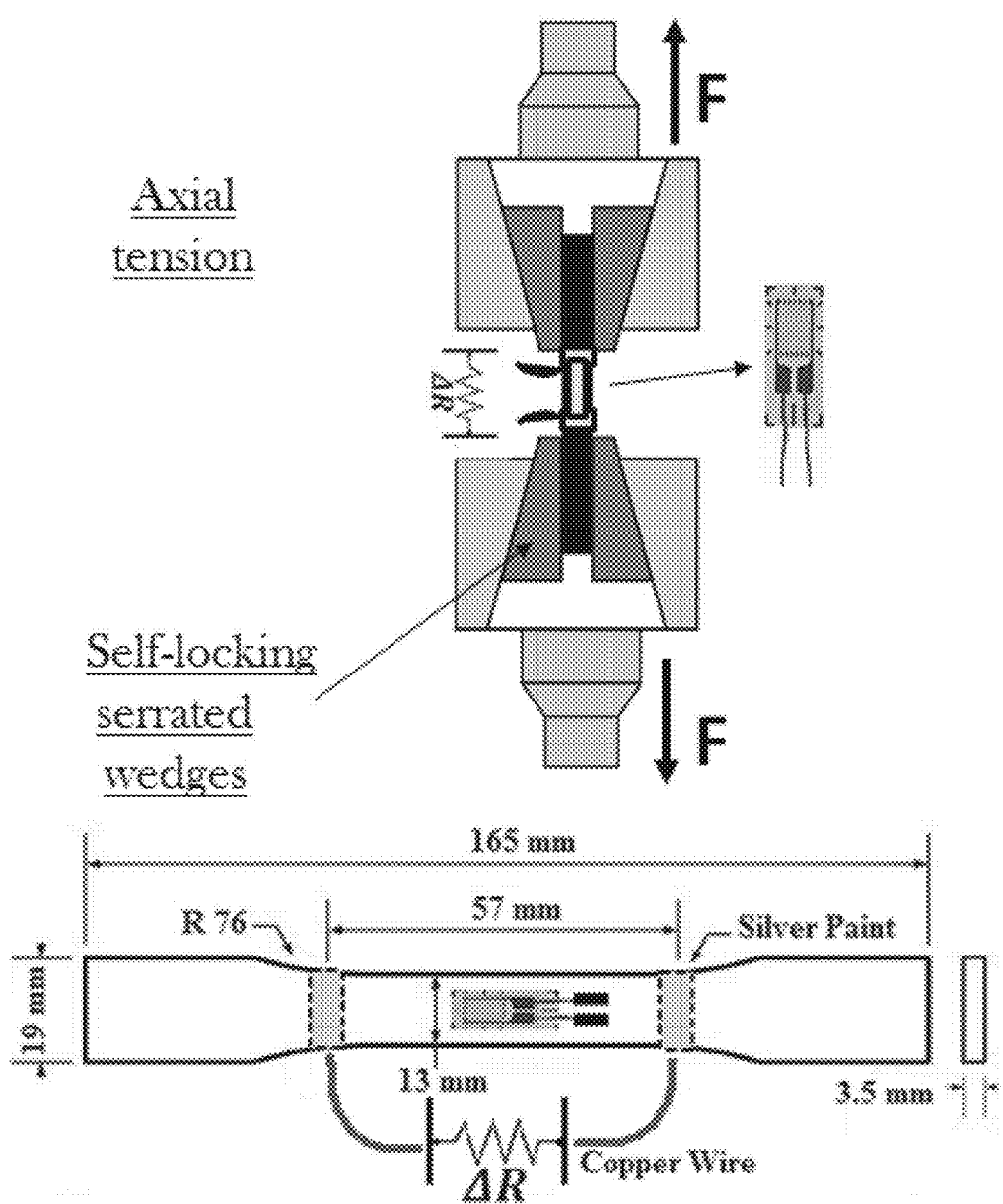
FIG. 1 schematically illustrates the test setup and the geometrical features of the specimens investigated for tensile tests.
Figure 2:
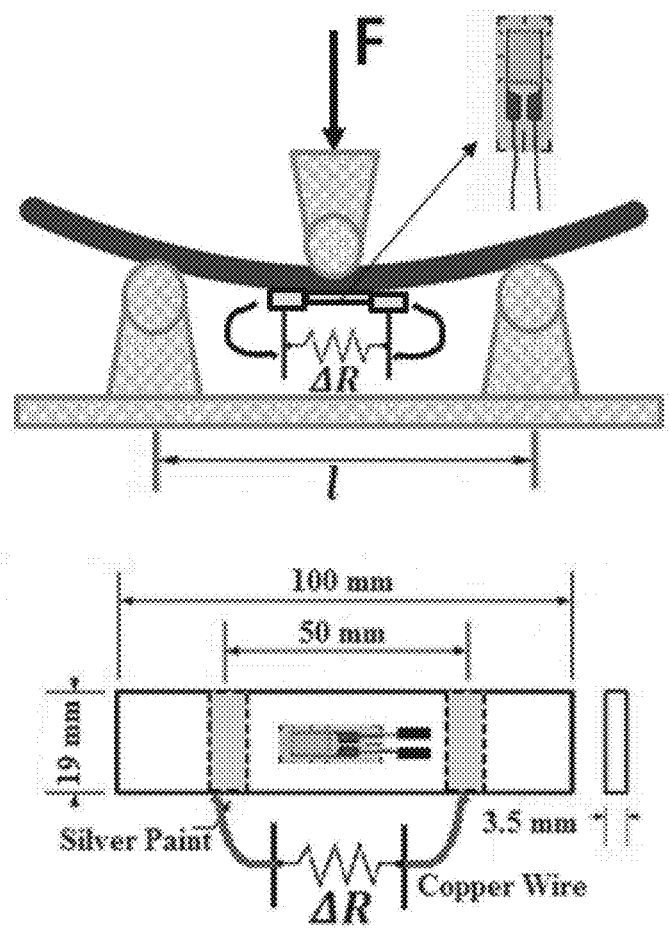
FIG. 2 schematically illustrates the test setup and the geometrical features of the specimens investigated for flexural tests.

An epoxy matrix was prepared by mixing an epoxy precursor, tetraglycidyl methylene dianiline (TGMDA) with an epoxy reactive monomer 1,4-butanediol diglycidyl ether (BDE) that acts as a reactive diluent. The curing agent adopted for this manufacturing process is 4,4-diaminodiphenyl sulfone (DDS). The epoxy mixture was obtained by mixing TGMDA with BDE monomer at a concentration of 80:20% (by weight) epoxide to flexibilizer. The hardener agent was added at a stoichiometric concentration with respect to all the epoxy rings (TGMDA and BDE). This particular epoxy formulation has proven to be very effective for improving nanofiller dispersion due to a decrease in the viscosity. In addition, it has been found to reduce the moisture content which is a very critical characteristic for aeronautic materials. Moreover, this epoxy formulation hardened with DDS is characterized by a good flame resistance with a limiting oxygen index of 27%, even without addition of antiflame compounds. Epoxy blend and DDS were mixed at 120° C. and the MWCNTs (3100 Grade purchased from Nanocyl S.A) were added and incorporated into the matrix by using an ultrasonication for 20 min (Hielscher model UP200S-24 kHz high power ultrasonic probe) in order to obtain a homogeneous dispersion. All the mixtures were cured by a two-stage curing cycles: a first isothermal stage was carried out at the lower temperature of 125° C. for 1 hour and the second isothermal stage at higher temperatures up to 180° C. or 200° C. for 3 hours. Samples micrographs were obtained with a field emission Scanning Electron Microscopy (SEM) apparatus (JSM-6700F, JEOL) instrument operating at 3 kV. Some of the nanocomposites section were cut from the solid samples by a sledge microtome. These slices were etched before the observation by SEM following a conventional procedure. In order to investigate the mechanical and piezoresistive behavior of the nanocomposites, axial and flexural response strength measurements were performed in agreement with ASTM standards D638 and D790, using a Dual Column Tabletop Testing Systems (INSTRON, series 5967) set with a cross head speed of 1 mm/min for both loading and unloading. In particular, for the flexural tests a configuration of a three point-bending mode was adopted. The corresponding force was measured by the machine load cell and converted to axial stress ($\sigma$), whereas mechanical strain ($\varepsilon$) was calculated as the machine crosshead displacement normalized by the gage length of the test specimen. In order to exclude possible slipping during the displacement, the local deformation was detected by means of a conventional strain gage (RS 5 mm Wire Lead Strain, gauge factor 2.1) to bonded to one side of the specimen and having a gauge resistance of 120$\Omega$ constantly measured with a precision multimeter HP 34401A. Copper electrodes were fixed on the sample surface using silver paint (Silver Conductive Paint, resistivity of 0.001 $\Omega$cm) thus ensuring a good ohmic contact between the parts for the measurement of the resistance, R, of the samples using the two-probe method with a Multimeter Keithley 6517A configured in the double function of voltage generator and ammeter. This measurement method, although simple, has successfully been applied in literature for resistance measurements in presence of tensile test. Contact resistance was neglected since the measured electrical resistance for all specimens was in the order of several k$\Omega$. The same electrodes were used for the impedance spectroscopy (IS) analysis performed with a precision LCR meter (model QuadTech 7600).

Preliminary Morphological and Electrical Characterization

Figure 3:
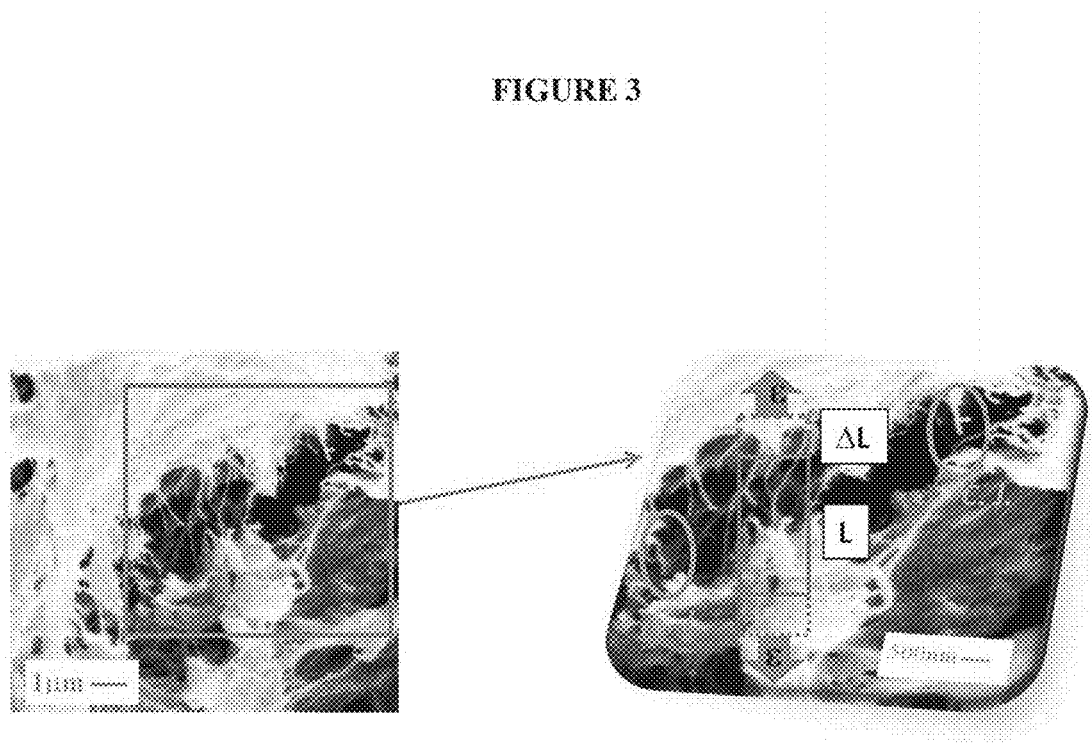
FIG. 3 illustrates SEM images of the fracture of composites with 0.3 wt. % loading of MWCNTs where possible conductive junction (CJ) are identified.

The strain sensing properties of the nanocomposites depend on the intrinsic response of the constituent materials (i.e., resin and MWCNTs) and on their mutual interactions which are governed by the interfacial properties. The distribution of the filler within the resin which determines the electrical percolation network and the formation of conductive junctions (i.e., CJ) due to the tunneling effect between neighbor tubes, can be highlighted by means of scanning electron microscopy (SEM) of a fractured surface of a nanocomposite, as shown in FIG. 3. In particular, the piezoresistivity behavior observed in the strain sensors based on CNT/polymer nanocomposites is attributable to relevant changes in the electrical network, e.g. loss of contact among CNTs, variation in the tunneling resistance due to the rearrangement of neighboring CNTs and intrinsic piezoresistivity of fillers due to their deformation. As a consequence, there is, in general, a new arrangement of the filler that results in small but experimentally detectable changes in the electrical properties.

A preliminary electrical characterization focused on the DC volume conductivity of the composites is carried out without applying any strain (0N) in order to identify a suitable filler concentration to be considered for testing under axial tension and flexural stress. Therefore in FIG. 4 the electrical conductivity ($\sigma$) as function of the amount of MWCNTs ($v$) is reported.

Figure 4:
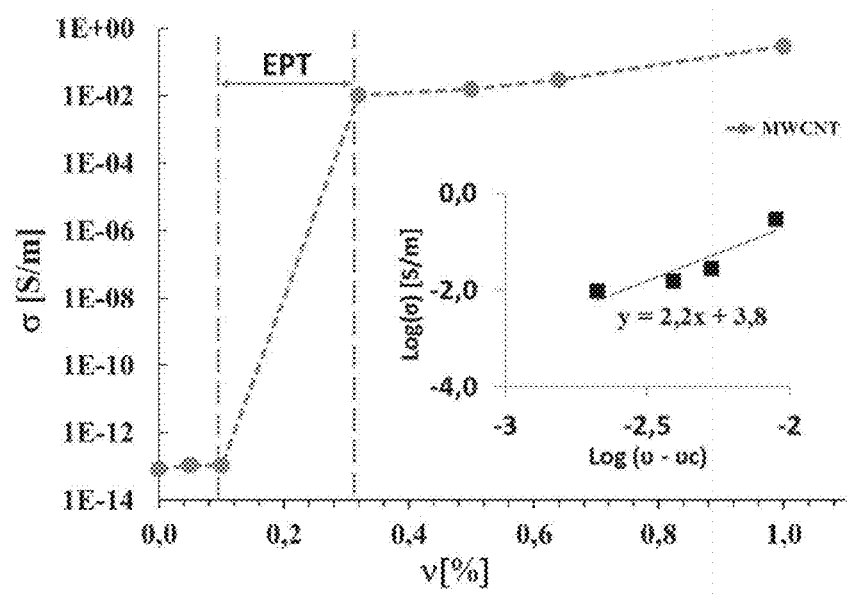
FIG. 4 illustrates a diagram of DC volume electrical conductivity ($\sigma$) versus MWCNT's weight percentage (v), with an inset showing the log-log diagram of the electrical conductivity as a function of (v–vc) with a linear fit.
Figure 5:
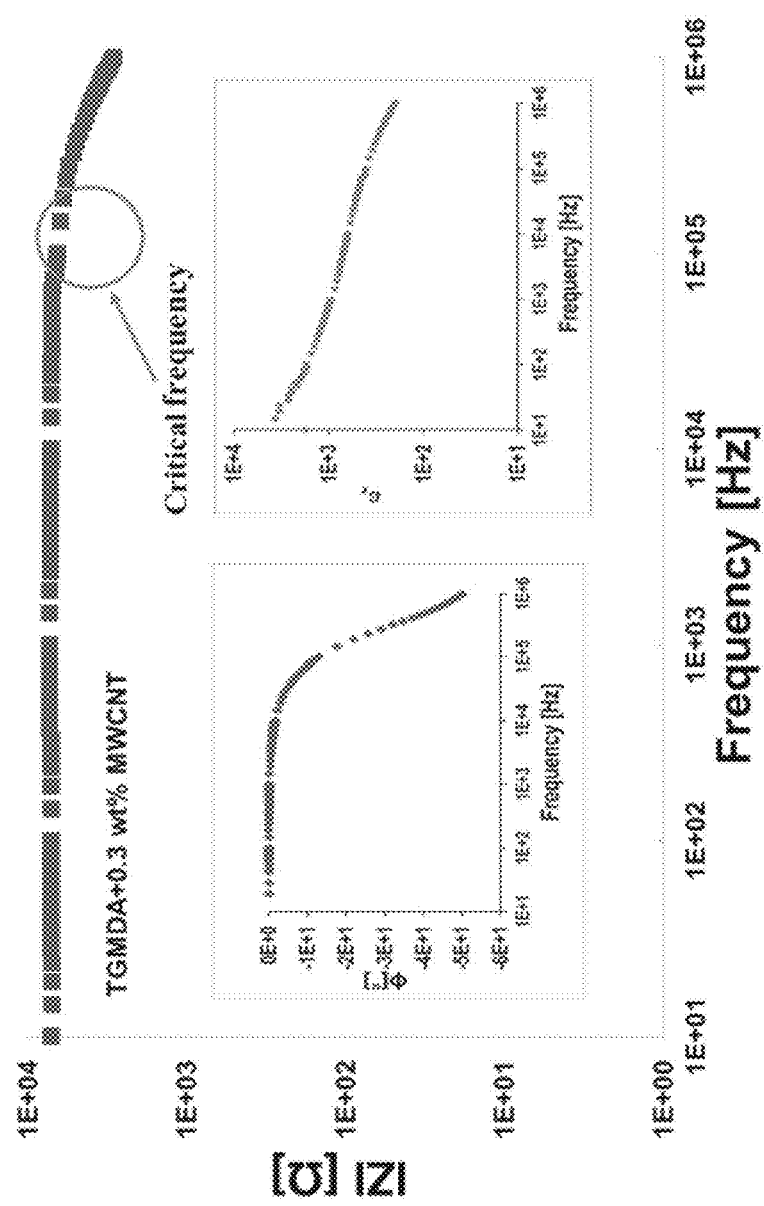
FIG. 5 illustrates a diagram of the modulus of impedance as function of frequency, with a circle highlighting the critical frequency, i.e. fc, and an inset showing the relative phase (degree) and the dielectric permittivity of the specimen vs. frequency.

As expected by the percolation theory, the conductivity depends on the filler loading in agreement with a scaling law of the type:

$$\sigma = \sigma_0 (v - v_C)^t \quad (1)$$

where $v_c$ is the amount corresponding to percolation threshold, $\sigma_0$ is the filler conductivity and t an exponent depending on the system dimensionality. In particular, conductive paths are formed in the composite when the CNT amount (i.e. $v$) increases over a threshold value (EPT, i.e. $v_c$) thus leading the material to convert from an insulating to a conductive behavior. It is worth to note that, as the concentration of the conductive fillers approaches the EPT, which is in the range 0.1-0.3 wt. %, an abrupt increase in the electrical conductivity of the composites, compared with the few pS/m characterizing the pure resin, can be observed. A value of about 0.29 S/m is achieved at the highest filler loading (i.e. 1 wt. %). The value of the exponent t (i.e. 2.2) of the percolation law, obtained as the slope of the linear interpolation in the inset of FIG. 4, is found to agree with universal values typically reported in literature. The sensitivity of the composites reinforced with carbon-base filler, as reported in different literature studies, is low when the composite acts as an insulator (below the EPT) and decreases significantly as the weight loading of CNTs increases in the high conductivity region. Therefore, the region around the EPT is the most suitable for sensor applications. Hence, according to the present method, the mechanical and piezoresistive tensile response of an epoxy resin suitable for the realization of structural aeronautic components and reinforced with 0.3 wt. % of multi-walled carbon nanotubes (MWCNTs) was investigated, when specimens are subjected to a low number of fatigue cycles in axial and flexural mode. Such specific filler concentration has been chosen since it is a first concentration above the EPT and because in aeronautical composites a good electrical conductance should be ensured. Furthermore, in order to explore the frequency response of the composite, impedance spectroscopy (IS) measurements are performed in the range 10 Hz-1 MHz without applying any strain (0N). FIG. 5 shows the plot of magnitude of the overall impedance of material (in $\Omega$) and in the inset the relative phase angle (in degree) and real part of the dielectric permittivity (i.e. $\varepsilon_r$) respectively, as a function of the frequency.

Such analysis allows to identify the critical frequency $f_c$ at which the electrical properties change from a frequency-independent to a dispersive (frequency-dependent) behaviour. In fact, it is interesting to note that up to 100 KHz the electrical behaviour exhibited by the composite is of resistive type since the impedance is almost constant and a phase about zero as for a resistor. Beyond this critical frequency, the capacitive effects mainly due to the insulating resin become dominant and the impedance varies with the frequency (i.e. f) following a trend described by Z whereas the phase $|Z| \sim 1/f$ whereas the phase $\Phi$ deviates from the null value to evolve, at higher frequencies, towards $-90°$ as for a typical insulating material equivalent from an electrical point of view to a capacitor.

Finally, the variations of the real part of the dielectric permittivity vs. frequency can be ascribed to the presence of free dipolar functional groups (mainly of type C—OH or sometimes N—H as reaction product) and more significantly to interfacial polarization attributable to the presence of conducting impurities. At low frequency the system shows the highest value and, as the frequency increases, the permittivity progressively decreases because both mechanisms become negligible.

DC Piezoresistive Characterization

Tensile Stress

Figure 6:
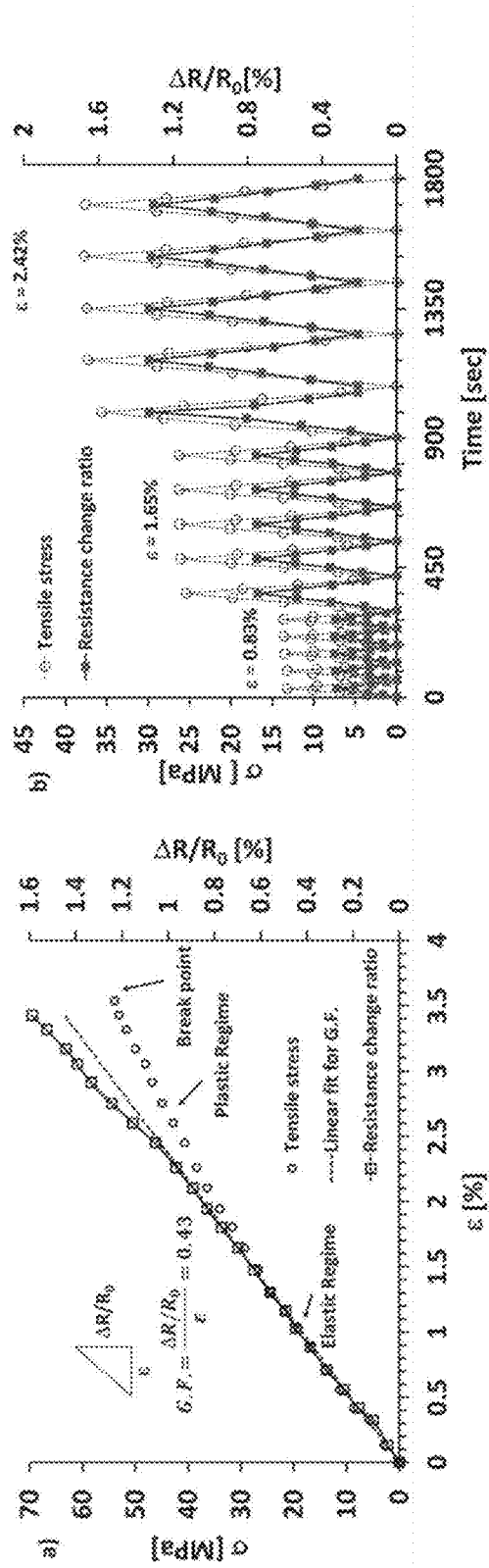
FIG. 6 illustrates two diagrams of mechanical behavior (i.e. $\sigma$, left vertical axis) and normalized change of electrical resistance (i.e. $\Delta R/R_0$, right vertical axis) observed in tensile stress as function of the axial strain ($\epsilon$) and vs. time for cycling tension loading of nanocomposites.

The left diagram of FIG. 6 shows the mechanical and piezoresistive performances of the epoxy-based composites reinforced with 0.3 wt % of MWCNTs when loaded in axial tension up to failure. In particular, the results concern the normalized change of electrical resistance $\Delta R/R_0$ (right vertical axis), where $R_0$ is the steady-state electrical resistance of the material without applying any strain (i.e. $\varepsilon = 0$) and $\Delta R = R - R_0$ is the instantaneous change in R, plotted against the axial strain (ε). The mechanical loading (i.e. σ) is also plotted on the left vertical axis. A direct relationship between the two plotted parameters can be observed. First of all, it is essential to identify the different operating regions such as the elastic one corresponding at lower strain levels (ε up to 2% with respect the rest position) which is followed by the plastic zone for higher loadings that gradually lead to the failure of the sample. In fact, at about 3.5% of strain we observe a cracking that discontinues the electrical measurements and leads to the specimen collapse, as shown in FIG. 6a). Therefore, the levels of strain in the subsequent experimental tests will be kept below this indicative critical value. In the first region corresponding to the elastic response of the material a linear mechanical behavior correlates with a linear piezoresistive curve as evident from the tangent plotted at the origin that coincide with the linear fit of such curves based on the first measured data points. Then, the $\Delta R/R_0$ curve becomes nonlinear with an evident abrupt change most likely due to the occurrence of the first nano-crackings within the structure. The sensitivity of a piezoresistive sensor, that is desirable to be as high as possible for practical applications, can be quantified in terms of gauge factor, a dimensionless parameter defined as the relative change in electrical resistance due to an applied strain (i.e. G.F.=$\Delta R/\varepsilon R_0$). The value obtained of 0.43 is derived as the slope of the interpolating line of $\Delta R/R_0$ curve of experimental data that lie in the elastic region. The increase of the overall resistance of the sample with increasing tensile stress agrees with the assumption that in a conductor-filled polymer the main electrical conduction mechanism occurs via "tunneling effect" which requires that the filler particles must be sufficiently close (at the so-called "tunneling distance") to each other to allow the electron flow. As a consequence of the imposed tensile strain, it is reasonable that the tunneling resistance could vary between neighboring CNTs due to the enlargement of inter-tube distance and/or a decreasing of the electrical contact areas. Both phenomena lead to an increase of the resistance exhibited by the sample. In order to investigate the reversibility and stability of sensor properties of the nanocomposites, specimens were subjected to tensile loading cycles based on increases/decreases of some selected level strains. As shown in the right diagram of FIG. 6, increasing strain per cycle was applied (i.e. 0.83%, 1.65% and 2.42%), and the temporal behavior of the piezoresistive response was monitored.

The resistive behavior of the sample is regular since, for the same value of the strain in each cycle, the variation of electrical resistance show comparable values of the $\Delta R/R_0$ ratio. It is worth noting that, when the crosshead returns to the initial position, for lower levels of strain that fall in the elastic regime (i.e. ε=0.83% and ε=1.65%). $\Delta R/R_0$ returns to zero after each loading cycle, indicating that significant permanent deformation or irreversible damage has not occurred in the composite. Otherwise, for higher value of tensile strain (i.e. ε=2.42%), when the deformation exceed the elastic response of the sample evolving toward the plastic one, it can be noted a change in resistance value that start to become irreversible for unloaded sample (i.e. σ=0). In particular, the presence of a residual resistance to appears due to some damage in the sensor most likely as a result of a permanent and irreversible phenomena (yielding) in electrical percolating network associated to morphological rearrangement of the CNTs dispersed in the polymer resin and to the fatigue and plastic deformation of the latter. Therefore, in plastic regime the sensor system may allow the detection of possible damages in the monitored part.

Flexural Stress

The change of electrical resistance was also correlated to bending deformations. Other literature studies report experiments performed in the 4-points-bending mode where the strain was calculated from the theory of pure bending of a plate due to a cylinder surface, valid between the inner loadings points. Here, the flexural stress-strain curves are obtained from three point bend test of the samples. The obtained results are shown in the left diagram of FIG. 7. In order to prevent possible discrepancies during the displacement, the flexural strain was detected by means of a conventional strain gauge. In Table I the experimentally detected values are also compared to those evaluated from the following relation:

$$\varepsilon_{flexural} = \frac{6Dt}{L^2} \qquad (2)$$

where D is the maximum deflection of the center of the sample (mm), t is the thickness of the sample (mm) and L is the support span (mm). From the analysis of the data in Table I it can be noted that the theoretical values are always lower than those achieved by measurement.

TABLE 1

Comparison of the flexural strains evaluated from theory and with a strain gauge

| $\varepsilon_{flexural}$ | [%] |
|---|---|
| Theory | 0.29-0.58-0.87-1.16-1.46-1.75-2.04-2.33-2.63-2.92 |
| Strain Gauge | 0.34-0.69-1.04-1.38-1.73-2.07-2.42-2.76-3.11-3.45 |

Figure 7:
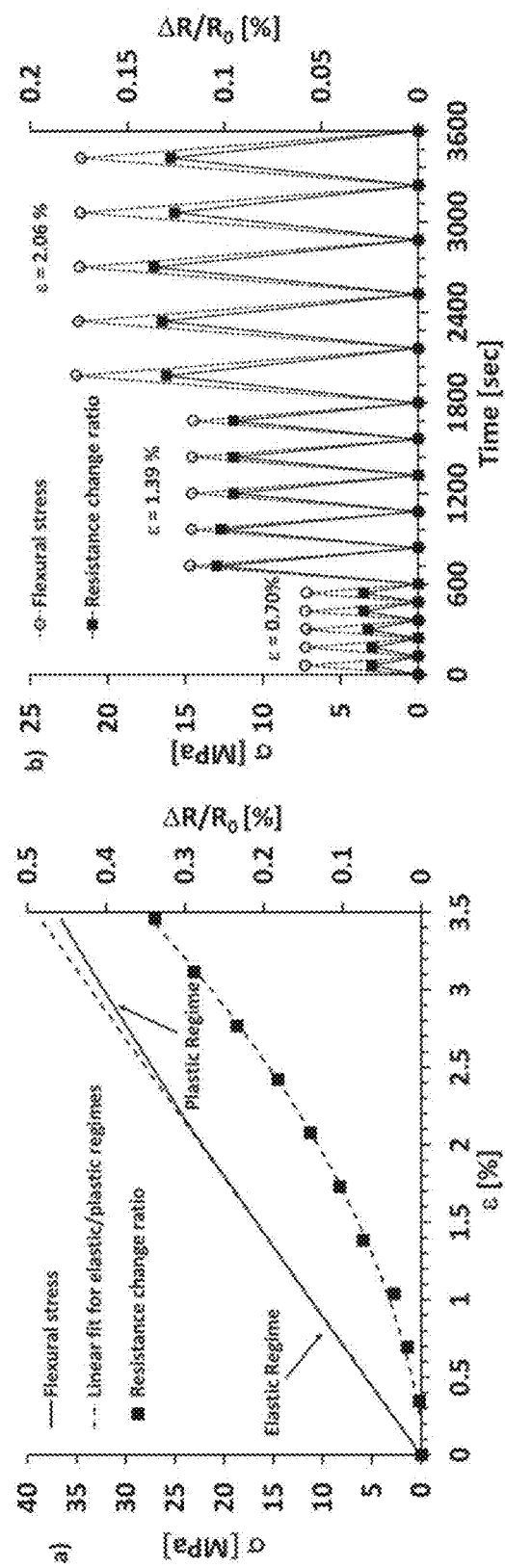
FIG. 7 illustrates two diagrams of mechanical behavior (i.e. $\sigma$, left vertical axis) and normalized change of electrical resistance (i.e. $\Delta R/R_0$, right vertical axis) observed in tensile stress as function of the axial strain ($\epsilon$) and vs, time for cycling tension loading of nanocomposites.

Differently from the piezoresistive behavior observed in tensile test, the normalized change of electrical resistance $\Delta R/R_0$ vs. strain measured in such mode is nonlinear in the whole strain range and follows an exponential law, as reported in the left diagram of FIG. 7. Also under flexural stress condition, different cycles in z-displacement with several level of strain were applied to the specimens. The mechanical behavior and change of electrical resistance as function of time were measured and correlated to strain, as shown in the right diagram of FIG. 7.

It is evident that the electrical resistance changes vary with the intensity of strain and that the maximum value achieved for each level of deformation is maintained for different cycles. Moreover, the resistance resumes its initial value under an applied strain up to 2.06% which, as indicated in the left diagram of FIG. 7, falls in the elastic regime. This reproducible resistive response during the mechanical cycles indicates that no ruptures or permanent deformation has occurred in the material structure.

Figure 8:
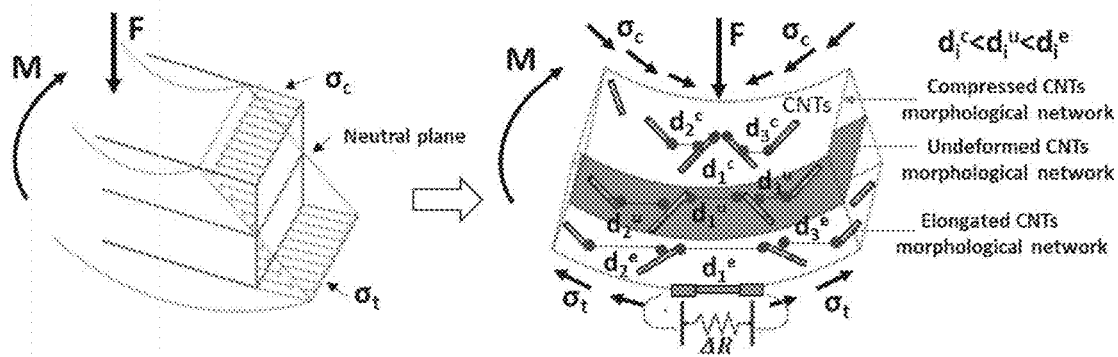
FIG. 8 illustrates the dynamic deformation in the case of bending stress (left) and geometrical effect on the CNTs morphological electrical network (right)

The different behaviors observed for the two types (tensile and flexural) of imposed stresses may be justified by considering Saint Venant's theory and Navier's formulas, under the hypothesis of plane and small deformations. In presence of tensile stress, i.e. the application of a traction force normal to the surface, the material reacts with a simple stretching in the direction of the force. As a result, the percolation network reacts with a uniform elongation of inter-particle distances. Instead, under flexural stress, the behavior may be attributed to an inflection giving a curvature according to an arc of circumference generated by the bending moment (i.e. M). As a consequence, in this case the electrical response of the material is influenced by a combination of two coexisting dynamic effects. In fact, following this inflection some parts (those above the neutral plane, i.e. $n_p$) of resin, which acts as an insulating spacer between the conductive particles, will shorten due to the action of the internal compressive stresses (i.e. $\sigma_c$) and other (those below the neutral plane) will lengthen due to internal tensile stresses (i.e. $\sigma_t$), as shown in FIG. 8. With the gradual increment of specimen curvature, due the increasing strain values, the elongation of resin in the convex part will predominate over the compression of the same in the concave part. As a result, the tunneling resistance between nanotubes, particularly sensitive to distance variations, affects more significantly the electrical response of the material thus originating the to exponential dependence of the $\Delta R/R_0$ vs. strain. Summarizing, there are two different effects that contribute to the results: the piezoresistive effect of the material and the geometric effect due to the type of applied force.

AC Piezoresistive Characterization
Tensile Stress

Figure 9:
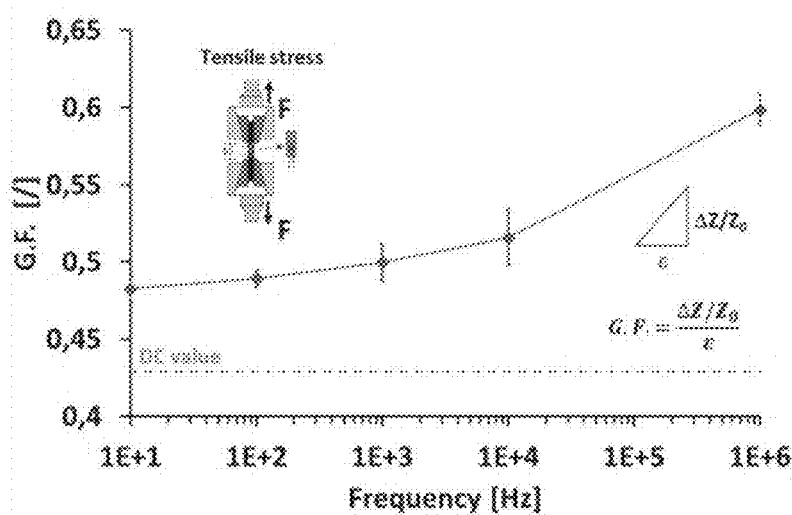
FIG. 9 illustrates a diagram sensitivity vs. frequency of a composite under tensile stress, wherein the markers refer to the average value of the measurements carried out on different specimens and the corresponding error bars are also reported.

The sensitivity of the composites evaluated with DC measurements has been also compared with that obtained by impedance analysis, in order to evaluate a possible contribution of the dielectric properties on sensing performances. In fact, from the preliminary AC investigation illustrated in FIG. 5, the impedance of the sample, starting from the frequency of 100 kHz was found to be dispersive (frequency dependent) due to capacitive effects that start to become dominant over those associated to the conduction, thereby influencing the macroscopic AC properties of the composites. The strain sensitivity of the composites under tensile loads in AC was investigated in terms of gauge factor (i.e. G.F.) defined as the normalized variation of the electrical impedance $\Delta Z/Z_0$ as function of the axial strain (i.e. $\varepsilon$) where $\Delta Z$ and $Z_0$ are the instantaneous change in the electrical impedance and its initial value before mechanical loading (i.e. ($\sigma=0$), respectively (see FIG. 9).

Figure 10:
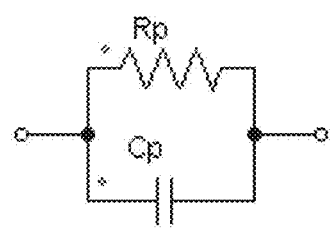
FIG. 10 illustrates the equivalent circuit for the electrical behavior of a nanocomposite.

It is possible to note that the G.F. improves significantly as the frequency increases and in particular the most favorable value is observed at 1 MHz where G.F. is 0.60, about 40% higher than that estimated in DC. This improvement in the sensitivity may be attributed to a synergy between the capacitive and resistive effects that coexist in a composite system with an insulating matrix filled with a conductive phase and that can magnify the response of the sensor. In fact, the AC properties of the polymer/carbon based composites can be analyzed by using a single-time-constant equivalent circuit model (i.e. STC circuit) whose overall impedance is given by the parallel combination of a resistor (i.e. Rp) and capacitor (i.e. Cp) as shown in the equivalent circuit of FIG. 10.

The relations between the impedance and the electrical parameters of the equivalent circuit are:

$$|Z| = \frac{R_p}{\sqrt{1+\omega^1 R_p^2 C_p^2}}, \varphi = \arctg(\omega R_p C_p) \quad (3)$$

to where, at first approximation, Rp takes into account the conduction via the CNT-particles percolative network (i.e. tunneling resistance, $R_{tun}$) and Cp takes into account the small but diffuse coupling capacitances between the neighboring CNTs separated by a thin insulating film and mainly the "background" dielectric behavior of the resin (i.e. $C_{res}$) which as a first approximation can be considered as that of a parallel-plate capacitor.

In particular, these electrical effects can be quantified according to the following expressions:

$$R_{tun} = \frac{h^2 d}{Se^2\sqrt{2m_e\lambda}} \exp^{\left(\frac{end}{h}\sqrt{2m_g 1}\right)}; C_{res} = \varepsilon_0 \cdot \varepsilon_{res} \cdot \frac{A}{d_z} \quad (4)$$

where h is the Plank's constant, e is the electron charge, $m_e$ is the mass of electron, $\lambda$ is the height of barrier, d and S are respectively the distance between conductive particles and the area involved in the tunneling phenomena approximated as the cross-sectional area of the CNTs, $\varepsilon_0$ and $\varepsilon_{res}$ are respectively the permittivity of free space and that of the neat resin, while A and $d_s$ are the area of plates and their separation.

Figure 11:
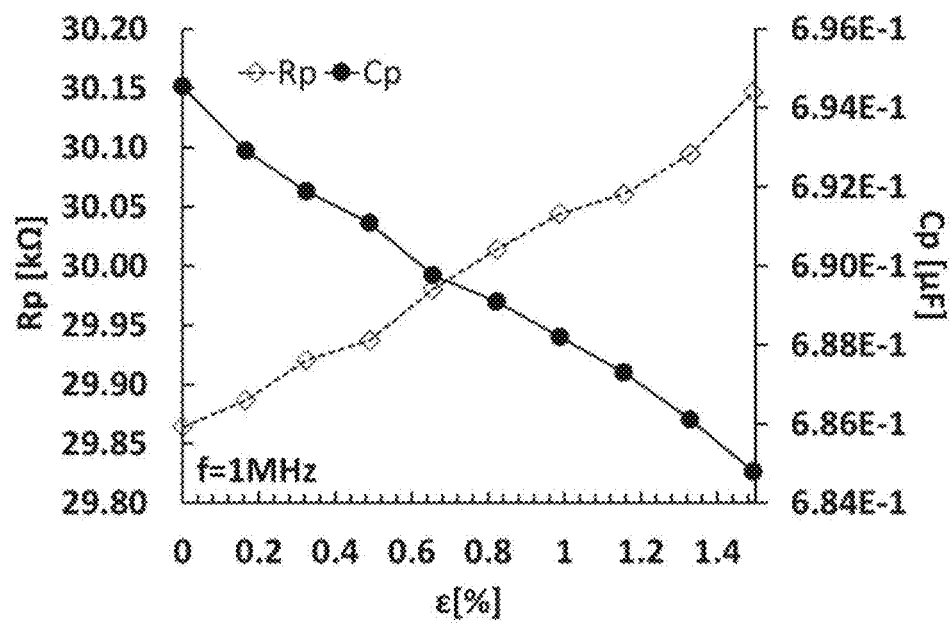
FIG. 11 illustrates a diagram of the resistance and capacitance variation of a sensor under different levels of strain for composites analyzed at f=1 MHz.

The tunneling resistance increases with the particle separation up to of a cut-off distance (about 2 nm); unlikely, the capacitance decreases as the particle distance increases. The changes in the values of resistances and capacitances of the sensor under different level of strain are analyzed at the frequency of 1 MHZ and the results are shown in FIG. 11.

Figure 12:
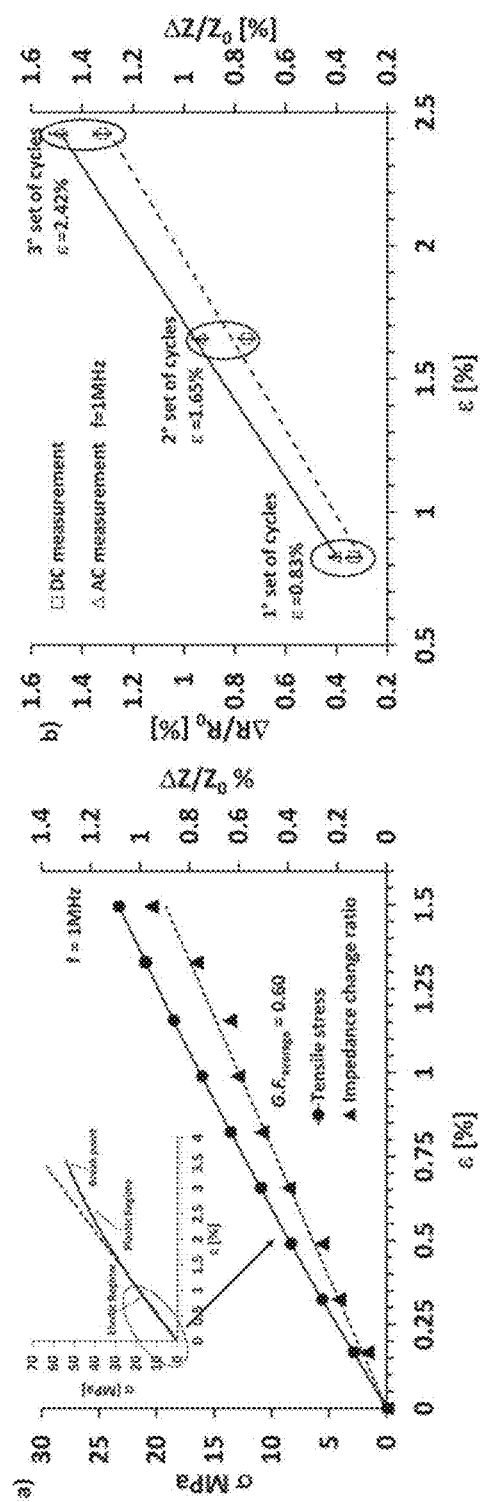
FIG. 12 illustrates two diagrams of sensitivity of a composite under tensile stress evaluated in the elastic range (left), and comparison of the sensitivity of the composite under tensile stress measured in DC and AC domain (right), wherein the markers refer to the average value of the measurements performed on different specimens and the corresponding error bars are also reported.

As expected, the distances between the conductive CNT-particles increase with the increment of strains and, as a consequence, Rp increases and Cp decreases Flexural Stress The left diagram of FIG. 12 shows the mechanical and piezoresistive response of the nanocomposites measured at operating frequency of 1 MHz when strain that falls in the elastic regime of the material is applied in order to evaluate the gauge factor. In particular, the results concern the normalized change of electrical impedance $\Delta Z/Z_0$ (right vertical axis), and that of mechanical loading (i.e. $\sigma$, left vertical axis) plotted against the axial strain ($\varepsilon$). It is possible to observe that $\Delta Z/Z_0$ increases linearly as a function of the tensile strain with $\Delta Z/Z_0 \sim k\varepsilon$ where k, coincident with the G.F. (i.e. 0.60), is the slope of the interpolating line of the $\Delta Z/Z_0$ curve and therefore representative of the piezoresistive tensile behavior of the composite. In order to analyze the dynamic durability in terms of mechanical integrity and electrical functionality, the endurance of strain sensors to subsequent stretching/releasing cycles at different level of strains is tested with AC measurements and the results are compared to the values obtained with DC investigations. In particular, the right diagram of FIG. 12 shows this comparison for the average values of both the maximum resistance and impedance change ratios measured at each level of strain during the different cycles. An evident increment appears if the strain is evaluated in terms of changes of impedance rather than that of resistance variations. In fact, regardless the level of strain, the sensor exhibits higher strain sensitivity in AC than in DC due to the additional contributions of the capacitive elements.

Figure 13:
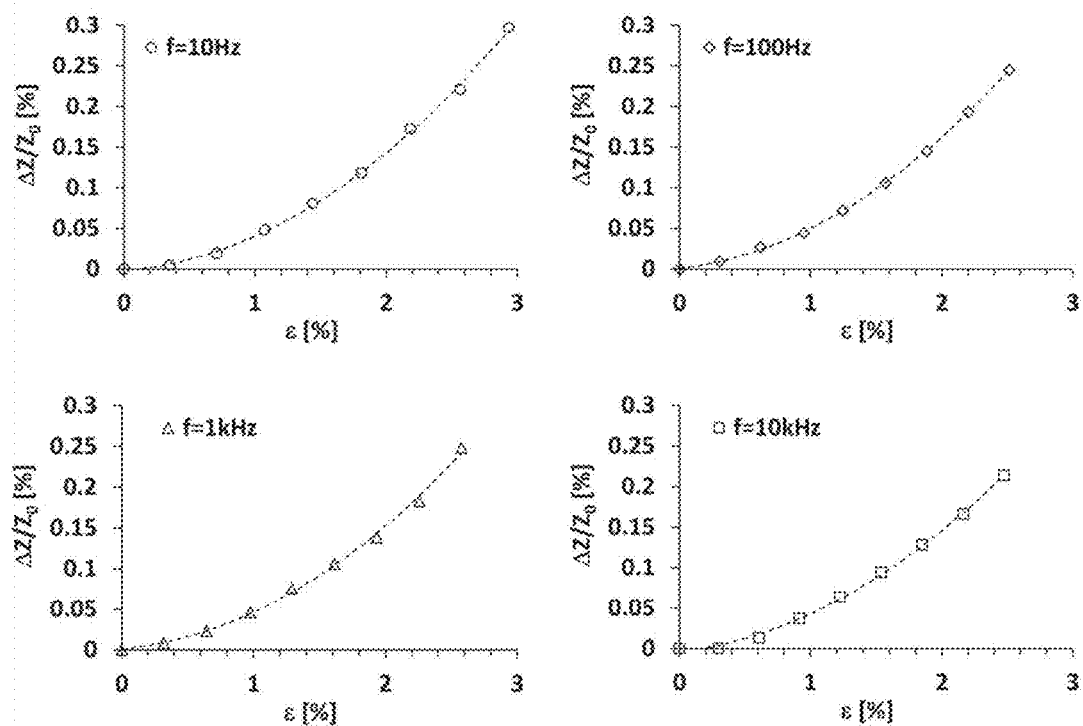
FIG. 13 illustrates four diagrams of behavior of normalized change of electrical impedance versus flexural stress at different operating frequencies.

FIG. 13 shows the experimental results concerning the piezoresistive response of the material, in terms of impedance changing ratio, when subjected to bending loads, evaluated at different operating frequency.

From the diagrams of FIG. 13, it is evident that the electrical response follows exponentially the mechanical deformation consistently with the results observed in DC. Given the nonlinearity of the curves, it is technically impossible to extrapolate a sensitivity index from such measures. After all, it would be meaningless because sensor nonlinearity could make the calibration process particularly difficult and complex. However, it is worth noting as shown in FIG. 13, how the concavity of the curve tends to become less pronounced with increasing frequency. The measurements carried out at the frequency of 1 MHz identified in the previous analysis are particularly interesting. In fact, at this frequency the behavior of the composite follows an almost linear trend with the mechanical stress. Therefore, in the left diagram of FIG. 14 the flexural stress (i.e. σ, left vertical axis) and normalized change of electrical impedance (i.e. $\Delta Z/Z_0$, right vertical axis) as function of the strain (ε) are shown. In this case, it is possible to fit the curves of the experimental data with a linear regression whose slope provides the G.F. of sensor for which a value of 1.28 is obtained.

Figure 14:
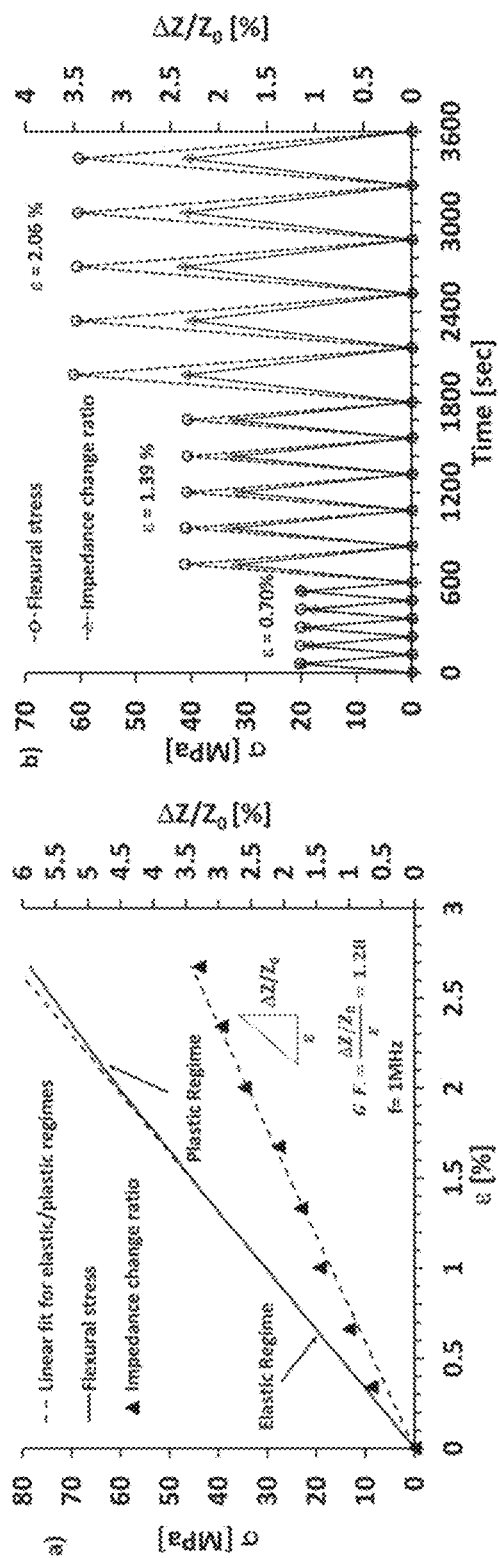
FIG. 14 illustrates two diagrams of mechanical behavior (i.e. $\sigma$, left vertical axis) and normalized change of electrical resistance (i.e. $\Delta Z/Z_0$, right vertical axis) observed in tensile stress as function of the axial strain ($\epsilon$) and vs. time for cycling tension loading of nanocomposites.

Moreover, following the same procedure described in the previous sections to verify the dynamic durability of the sensor, AC measurement are carried out on the specimens and the results are reported in the right diagram of FIG. 14.

The electrical response of the sample is regular since the impedance variations, at the same value of the strain, exhibits comparable values (%) in the ratio $\Delta Z/Z_0$. Furthermore, the electrical response follows linearly the mechanical deformation, both during the loading and the unloading phases. Since the deformation loads are limited in the elastic regime of the material (about 2%), $\Delta Z/Z_0$ returns to the initial value after each loading cycles thus indicating that the applied strain induces reversible variations in the nanotube network configuration.

Figure 15:
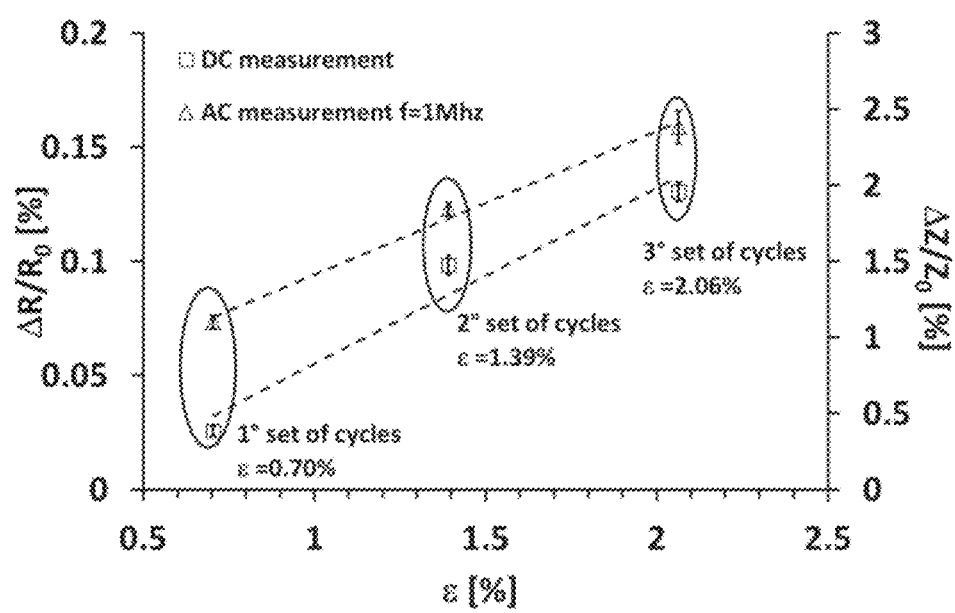
FIG. 15 illustrates a diagram of comparison of the sensitivity to strain of a composite evaluated with DC and AC measurements, wherein the markers refer to the average value of the measurements performed on different specimens and the corresponding error bars are also reported.

Finally, as illustrated by FIG. 15, the resistance and impedance change ratios (i.e. $\Delta R/R_0$ and $\Delta Z/Z_0$, respectively) are compared for each level of strain in terms of average of the maximum value measured in each cycle.

It is interesting to note that in flexural mode there is a remarkable difference, greater than two order of magnitude, if the strain is detected in terms of variation of impedance rather than resistance. In fact, if the small strain of 0.7% applied to the sample induces a resistance change ratio of only 0.2%, the same strain leads to a variation of impedance change ratio of 1.1%. The sensitivity vs. strain is about 108 times greater for the measurements performed in AC with respect to those in DC.

It shall be apparent that, applying the principles of the invention, the implementation details and the embodiments may be widely varied relative to what has been described by way of example only, within the scope defined by the following claims.

The invention claimed is:

1. A method for monitoring a composite material constituting an aircraft structure comprising an epoxy resin filled with electrically conductive nanoparticles, at least one electrical property of said composite material being influenced by being subjected to a mechanical deformation, said method providing for inserting said composite material in an electric circuit emitting an electric signal whose value depends on said electrical property, so that, when the value of said signal overcomes a given threshold value, a warning message is delivered, wherein said electrical property is the electrical impedance, and said warning message is delivered when a crack of at least 1 nm is formed within said aircraft structure.

2. The method according to claim 1, wherein said electrical property is the overall electrical impedance of the composite material constituting a structural element.

3. The method according to claim 1 or 2, wherein said electric circuit is subject to an electrical tension in the range 1 mV to 220 V, and preferably in the range 1 mV to 20V.

4. The method according to claim 1 or 2, wherein said warning message is a visual and/or acoustic message.

5. The method according to claim 1 or 2, wherein said electrical circuit is fed with AC.

6. The method according to claim 5, wherein said AC has a frequency in the range 1 Hz to 1 GHz.

7. The method according to claim 1 or 2, wherein said electrically conductive nanoparticles are multi-walled carbon nanotubes (MWCNTs).

8. The method according to claim 1 or 2, wherein said electrically conductive nanoparticles are carbon nanofibers or graphene-based nanoparticles, in particular graphene single layers, graphene layers or exfoliated graphite.

9. The method according to claim 1 or 2, wherein said electrically conductive nanoparticles constitute 0.01 to 5% by weight of the total weight of said composite material.

10. The method according to claim 1 or 2, which is a real-time self-health monitoring method of a structure, in particular an aircraft structure, incorporating said composite material.

11. The method according to claim 1, wherein said crack is up to 5 nm.

12. The method according to claim 1, wherein a Young's modulus of said composite material is in the range 500 to 3000 MPa at room temperature.

13. A method for monitoring a composite material constituting an aircraft structure comprising an epoxy resin filled with electrically conductive nanoparticles, at least one electrical property of said composite material being influenced by being subjected to a mechanical deformation, said method providing for inserting said composite material in an electric circuit emitting an electric signal whose value depends on said electrical property, so that, when the value of said signal overcomes a given threshold value, a warning message is delivered, wherein said electrical property is the electrical impedance, and a Young's modulus of said composite material is in the range 500 to 3000 MPa at room temperature.

14. The method according to claim 13, wherein said electric circuit is subject to an electrical tension in the range 1 mV to 220 V, and preferably in the range 1 mV to 20V.

15. The method according to claim 13, wherein said warning message is a visual and/or acoustic message.

16. The method according to claim 13, wherein said electrical circuit is fed with AC.

17. The method according to claim 16, wherein said AC has a frequency in the range 1 Hz to 1 GHz.

18. The method according to claim 13, wherein said electrically conductive nanoparticles are multi-walled carbon nanotubes (MWCNTs).

19. The method according to claim 13, wherein said electrically conductive nanoparticles are carbon nanofibers or graphene-based nanoparticles, in particular graphene single layers, graphene layers or exfoliated graphite.

20. The method according to claim 13, wherein said electrically conductive nanoparticles constitute 0.01 to 5% by weight of the total weight of said composite material.

* * * * *